United States Patent [19]

Diamond

[11] Patent Number: 4,483,854

[45] Date of Patent: Nov. 20, 1984

[54] SYSTEMIC TREATMENT OF PSORIASIS USING CERTAIN SALICYLATES

[75] Inventor: Julius Diamond, Mountain Lakes, N.J.

[73] Assignee: Key Pharmaceuticals, Inc., Miami, Fla.

[21] Appl. No.: 484,387

[22] Filed: Apr. 12, 1983

[51] Int. Cl.³ .............................................. A61K 31/60
[52] U.S. Cl. ..................................... 424/230; 424/231
[58] Field of Search ................................ 424/230, 231

[56] References Cited

PUBLICATIONS

Chemical Abstracts 81:54414d (1974).
Chemical Abstracts 77:130609f (1972).

*Primary Examiner*—Leonard Schenkman
*Attorney, Agent, or Firm*—Wegner & Bretschneider

[57] ABSTRACT

Psoriasis is systemically treated by the administration of a salicylate which is capable of inhibiting the endogenous lipoxygenase present in psoriatic plaque fluid without the inhibition of the cyclooxygenase enzyme.

6 Claims, No Drawings

SYSTEMIC TREATMENT OF PSORIASIS USING CERTAIN SALICYLATES

Psoriasis is systemically treated in accordance with this invention by introduction into the bloodstream of a salicylate which is capable of inhibiting the endogenous lipoxygenase present in psoriatic plaque fluid without inhibition of the cyclooxygenase enzyme. This invention includes both a method of treatment and a composition or dosage form suitable for administration to a patient suffering from psoriasis.

High levels of arachidonic acid and 5-HETE are known to be associated with psoriasis, while levels of $PGE_2$ are only slightly elevated. Thus, the cyclooxygenase pathway in psoriatic lesions is greatly inhibited, while 5-lipoxygenase and 12-lipoxygenase pathways are encouraged. It appears that an inhibitor of cyclooxygenase is present in psoriatic lesions which causes the disposition of arachidonic acid to be redirected via the lipoxygenase pathway. The transformation of arachidonic acid to $LTB_4$ and 5-HETE in the epidermis is catalyzed by the 5- and 12-lipoxygenases. Aspirin, the most widely prescribed and best known salicylate, acts to inhibit the cyclooxygenase pathway and will exacerbate psoriasis.

In accordance with this invention a systemic treatment of psoriasis and dosage form for this treatment is provided by the use of certain salicylates, which I have found are relatively ineffective inhibitors of cyclooxygenase and thus have little inhibitory effect on the biosynthesis of $PGE_2$. At the same time, however, the salicylates of this invention will inhibit the lipoxygenases and thereby interfere with the biotransformation of arachidonic acid to $LTB_4$ and 5-HETE.

Acceptable salicylates include salicylic acid and salicylic acid derivatives, such as salicylsalicylic acid and 5-(2',4'-difluorophenyl)salicylic acid. In preferred embodiments, pharmaceutically acceptable salts are used, such as the choline, sodium, magnesium or calcium salts thereof. In one embodiment, a substantially equimolar mixture of the calcium and magnesium salts of salicylic acid can be used. Because of the adverse properties of acetylsalicylic acid as discussed above, it is a requirement of any salicylate useful in this invention that its 2-hydroxy position be free from etherification or acetylation.

The method of this invention is practised by oral administration of the composition of this invention, which comprises a dosage of acceptable salicylate sufficient to raise blood levels to an effective amount, generally within the range of from about 200 to about 1200 mg per each six to twelve hour period, and preferably from about 350 to about 750 mg per each such period. The composition can be made up in tablets, capsules or other suitable oral dosage form, along with conventional carriers and excipients. Because of the relatively long life in the bloodstream of the salicylates of this invention, only a single oral dose each six to twelve hours is necessary.

What is claimed is:

1. A method of treating a patient suffering from psoriasis comprising orally administering to said patient an amount of a salicylic acid or a pharmaceutically acceptable salt of a salicylic acid effective to inhibit the endogenous lipoxygenase present in psoriatic plaque fluid without inhibition by cylcooxygenase enzyme, said salicylic acid being selected from the group consisting of salicylic acid, salicylsalicylic acid, and 5-(2',4'-difluorophenyl)salicylic acid.

2. The method of claim 1 wherein the acid is salicylic acid.

3. The method of claim 1 wherein the salt is calcium bis(salicylate).

4. The method of claim 1 wherein said acid or salt is salicylsalicylic acid or a pharmaceutically acceptable salt thereof.

5. The method of claim 1 wherein said acid or salt is 5-(2',4'-difluorophenyl)salicylic acid or a pharmaceutically acceptable salt thereof.

6. A method of treating a patient suffering from psoriasis comprising orally administering to said patient an amount of a substantially equimolar mixture of magnesium bis(salicylate) and calcium bis(salicylate) effective to inhibit the endogenous lipoxygenase present in psoriatic plaque fluid without inhibition of cylcooxygenase enzyme.

* * * * *